US00PP10554P

United States Patent [19]

Bjorge et al.

[11] Patent Number: Plant 10,554

[45] Date of Patent: Aug. 18, 1998

[54] 'FA 18' PEACH TREE

[75] Inventors: Annette Bjorge; Randy Bjorge, both of Coloma, Mich.

[73] Assignee: International Plant Management, Lawrence, Mich.

[21] Appl. No.: 738,258

[22] Filed: Oct. 28, 1996

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new peach variety, *Prunus persica*, (hereinafter referred to as the FA 18 peach tree) which was developed by Annette and Randy Bjorge in a breeding program at Fruit Acres Farm in Coloma, MI, having the following combination of unique and desirable features:

1. A fruit with excellent shipping and storage qualities.
2. A fruit maturing 30 days later than the 'Redhaven' peach.
3. A substantially round peach with white flesh and an attractive deep pinkish-red blush over a pinkish-white background covering 90% of the fruit at maturity.
4. A fruit with flesh that does not brown when cut.
5. A fruit and tree with resistance to Bacterial Spot.
6. A fruit and blossom that is very hardy.

3 Drawing Sheets

ORIGIN OF THE VARIETY

The new variety of peach tree FA 18 was developed by Annette and Randy Bjorge in a peach breeding program at Fruit Acres Farms, 2559 Friday Road, Coloma, Mi. 49038. The FA 17 peach tree was developed as a first generation cross between 'Fayette' and 'Newhaven', two established, non-patented, commercial varieties. The parent tree was grown and maintained in a peach tree breeding orchard in Fruit Acres Farms.

This new and distinct variety of peach tree has been asexually propagated by budding at Fruit Acres Farms in Coloma, Mich. The asexual propagation demonstrated that such reproduction of the characteristics of the tree are consistent and are established and transmitted through succeeding generations.

SUMMARY OF THE VARIETY

The new and distinct variety of peach tree is of large, vigorous, upright growth with medium density and is regular and productive bearer of peaches. The fruit of the new variety is characterized by its round, high shouldered, substantially 80% deep pinkish-red fruits with white flesh that present a very attractive appearance. The fruits have firm flesh and are resilient to the extent that they may be handled and packaged mechanically without damaging the same for shipment. This results in less spoilage and a greater market value. The flesh of the fruits of the new variety does not brown when cut. The fruits of the new variety have a recessed pistil point which avoids damage during picking and handling. The tree and fruits of the new variety exhibits resistance to Bacterial Spot. The fruit matures in the middle of the peach growing season in Southwestern Michigan. It ripens 30 days after the established commercial variety, 'Redhaven'.

BRIEF DESCRIPTION OF THE PHOTOGRAPHS

The accompanying photographs show typical specimens of the new variety in color as nearly true as it is reasonably possible to make the same in color illustrations of this character. The specimens were photograhed in Van Buren and Berrien counties of Southwestern Michigan.

Figure 1:
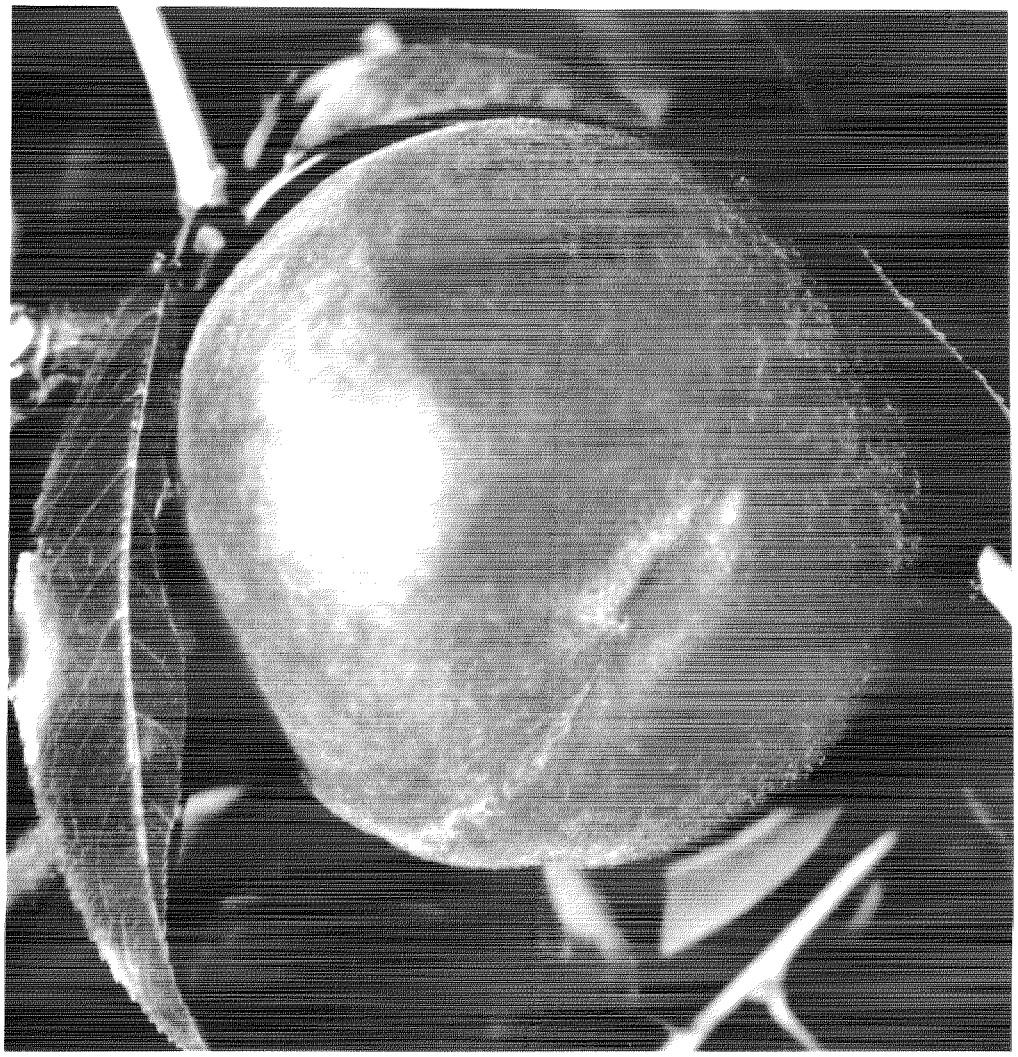
FIG. 1 illustrates specimens of the fully ripened fruit and foliage of the new variety.
Figure 2:
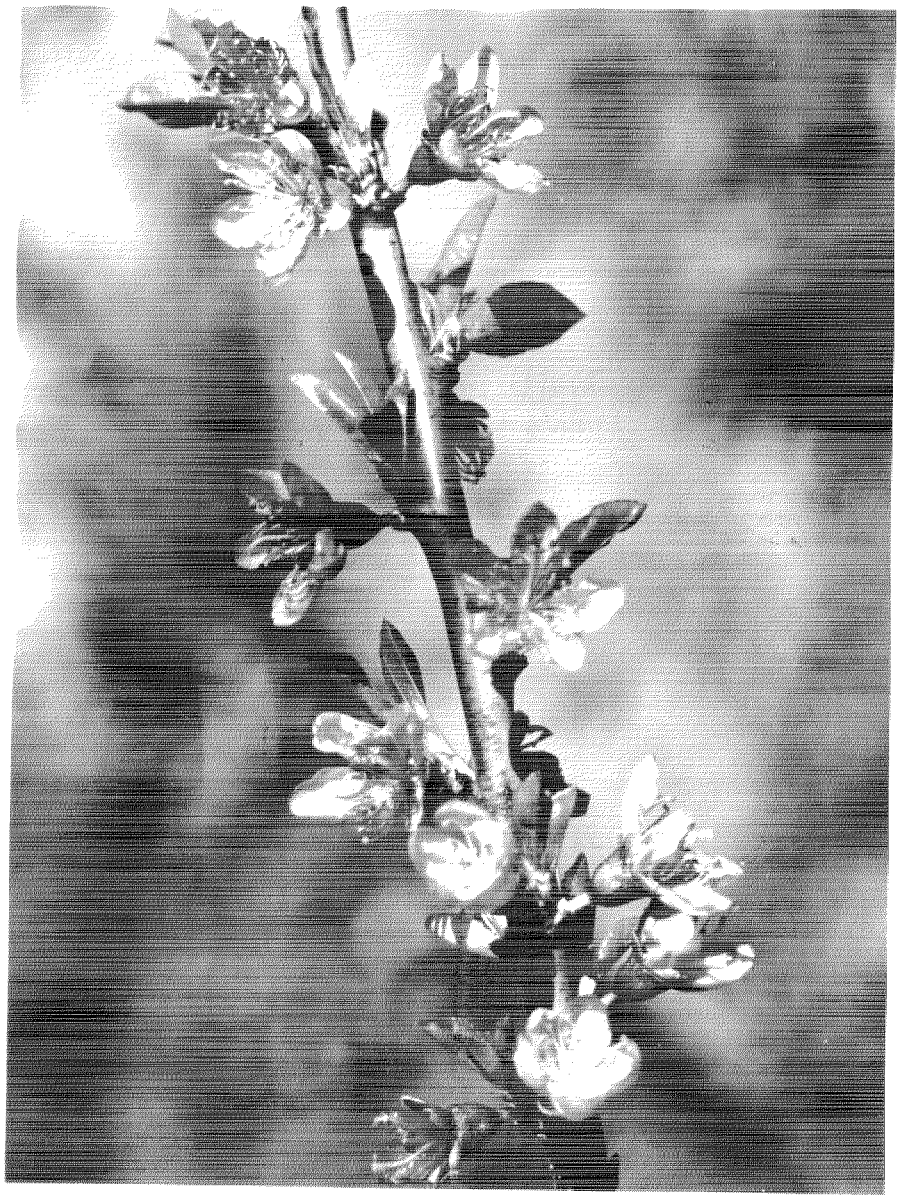
FIG. 2 illustrates blooms of the new variety.
Figure 3:
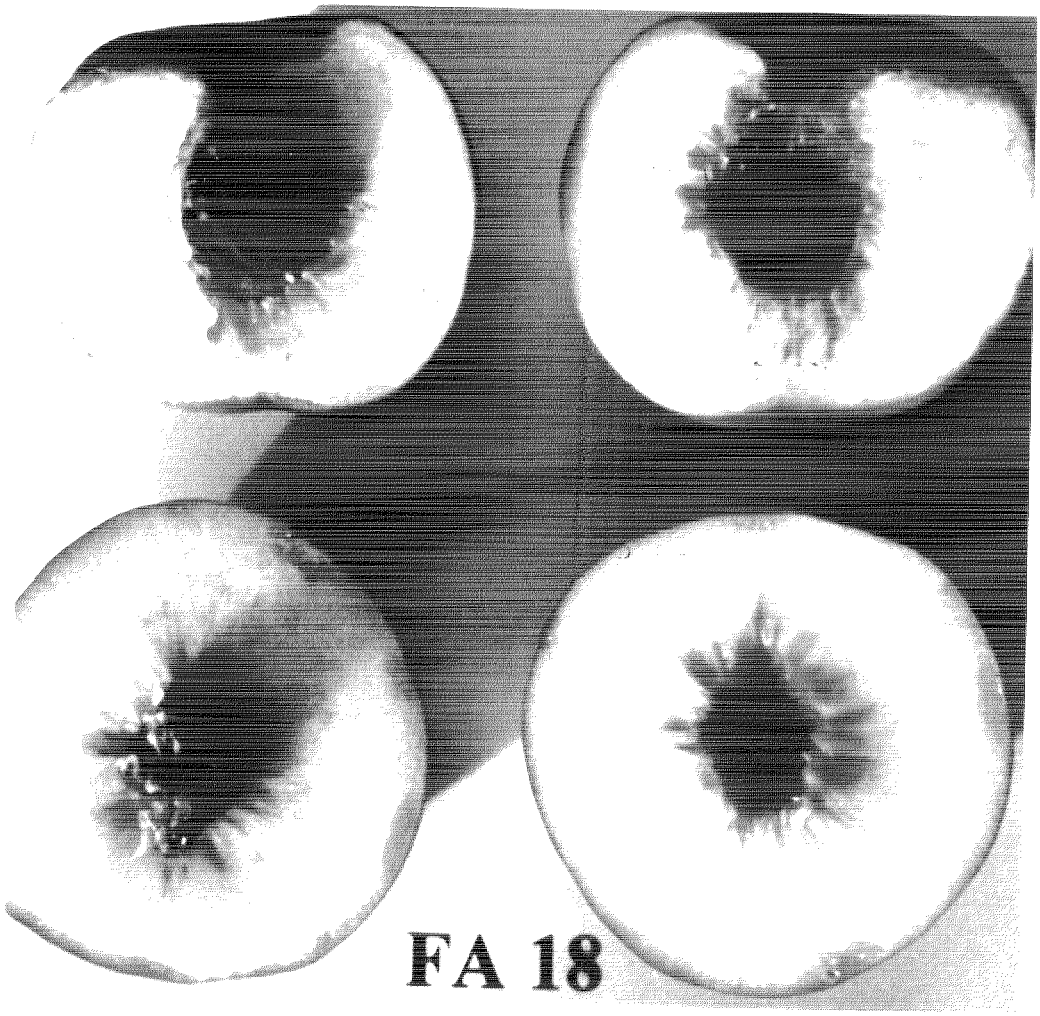

FIG. 3 Illustrates two specimens of the new variety. The upper specimen is bisected along the suture, the lower specimen is bisected as a ninety-degree angle to the plane of the suture. The color and forms of the flesh, pit and pit cavity are illustrated.

DETAILED DESCRIPTION OF THE VARIETY

The following description of the fruit and foliage of the new variety is based on observations of specimens grown in Berrien and Van Buren County of southwestern Michigan. The color terminology is in accordance with The Royal Horticultural Society Colour Chart, published by The Royal Horticultural Society of London, England.

Tree:

*Age of specimen.*—15 years

*Height.*—Unpruned 4.9M.

*Width.*—Unpruned 5.5 M..

*Size.*—Large.

*Vigor.*—Moderate, it requires early, diligent thinning and annual spring pruning.

*Density.*—Open, internode length averages 1 ½ to 2 cm.

*Form.*—Upright, spreading. The major scaffold branches form 45 to 55° angles to the trunk. It will form a central leader if left unpruned. It does not require supplemental support.

*Production.*—Heavy, ripens in 2 pickings with 70% of the crop mature in the first picking and 30% of the crop mature for the second picking. Is more productive that its parents and will produce up to 500 bushels per acre in an average year in Southwestern Michigan.

*Bearing.*—Annual, the mature fruits will hold on the tree for 7 days.

*Disease resistance.*—Some resistance to bacterial spot.

*Color hardiness.*—Very hardy.

Trunk:

*Size.*—Large.

*Surface.*—Smooth.

*Lenticils.*—Medium.

*Color.*—Gray 212 C..

Leaves:

*Size.*—Length 155 mm, width 41 mm.

*Form.*—Lanceolate, pointed.

*Thickness.*—Medium.

*Texture.*—Medium.

*Margin.*—Crenate.

*Petiole.*—Length 6–10 mm, thickness 1 mm.

*Glands.*—Reniform, 3 to 4 in number, located on upper petiole and lower leaf margin.

*Color.*—Upper surface green 147 A, lower surface green 147 B.

*Stipules.*—None.

Flower buds:

*Size.*—Medium.

*Length.*—Medium.

Flowers:

*Blooming period.*—Apr. 8 to 15 in Coloma, Mich.

*Presentation.*—Medium showy.

*Pollen.*—Present, self fertilizing.

*Petals.*—5 in number, length 7 mm, width 5 mm, Red-purple 73 A.

*Stamens.*—28 in number, slightly curved, 10 to 14 mm long.

*Pistil.*—Extends slightly beyond petals, white 155 A.

Fruit:

*Maturity when described.*—Firm ripe.

*Date of first picking.*—Sep. 1, in Southwestern, Mich. Harvest season lasts 5 days.

*Size.*—65 to 75 mm.

*Form.*—Round.

*Suture.*—Indistinct, clean.

*Pistil point.*—Inverted.

Skin:

*Thickness.*—Thin..

*Texture.*—Fine.

*Tendency to crack.*—None.

*Down.*—Slight.

*Color.*—90% Red 53 A blush combined with some mottling of red 52 A over a background of yellow-orange 18 C.

Flesh:

*Texture.*—Very fine.

*Aroma.*—Strong, pungent with the distinctive aroma of a white peach.

*Fibres.*—few, small, tender, not conspicuous or noticeable in eating.

*Color.*—White 155 B.

*Coloration at the pit.*—Bright reddish pink bleeding into the flesh around 80 to 90% of the pit cavity.

*Eating quality.*—Excellent, very high sweetness with medium acid.

Stone:

*Size.*—Length 35 mm, width 24 mm, thickness 18 mm.

*Form.*—Ovate.

*Apex.*—Pointed

*Sides.*—Nearly equal.

*Base.*—Straight to slightly slanted, wide.

*Surface.*—Pitted to furrowed throughout.

*Color.*—Grayed-Purple 183 A.

*Type.*—Freestone.

*Tendency to crack.*—None.

Use: Desert, fresh and commercial market.

Shipping quality: Excellent, can be handled like a yellow fleshed variety.

Keeping quality: Excellent, will hold 4 weeks in common cold storage.

Disease resistance: moderate resistance to bacterial spot.

We claim:

1. A new and distinct variety of peach tree, *Prunus persica*, substantially as herein shown and described, characterized particularly as to novelty by the unique combination of vigorous, upright, open, very hardy, large, medium density, regular bearing tree, with moderate resistance to bacterial spot, producing freestone fruits having clear white, non-browning flesh and substantially round, firm, 90% bright pinkish-red skin color at maturity which occurs 30 days after 'Redhaven' peach.

* * * * *